United States Patent [19]

Rozsa et al.

[11] 4,258,010
[45] Mar. 24, 1981

[54] SOLVENT EXTRACTION APPARATUS

[75] Inventors: László Rózsa, Miskolc I; Lajos Mészáros, Szeged; Ferenc Mogyorodi, Miskolc I, all of Hungary

[73] Assignee: Északmagyarországi Vegyimü vek, Sajóbábony, Hungary

[21] Appl. No.: 849,448

[22] Filed: Nov. 7, 1977

Related U.S. Application Data

[60] Continuation of Ser. No. 633,172, Nov. 19, 1975, abandoned, which is a division of Ser. No. 306,059, Nov. 13, 1972, Pat. No. 3,936,489.

[51] Int. Cl.$^3$ .............................................. B01D 11/04
[52] U.S. Cl. .................................................... 422/257
[58] Field of Search .................... 203/197, 153, 90, 39; 159/4 R, 4 A, 4 K; 422/256, 297

[56] References Cited

U.S. PATENT DOCUMENTS

| | | | |
|---|---|---|---|
| 305,631 | 9/1884 | Polk | 202/197 |
| 1,277,931 | 9/1918 | Heuser | 202/197 |
| 1,993,886 | 3/1935 | Jaeger | 203/90 |
| 2,232,544 | 2/1941 | Loving | 203/90 |
| 2,502,485 | 4/1950 | Saunders | 203/90 |
| 2,691,625 | 10/1954 | Clarke | 203/90 |
| 3,014,861 | 12/1961 | Buningh | 422/211 |
| 3,332,748 | 7/1967 | Betts | 422/211 |

FOREIGN PATENT DOCUMENTS 1296818 11/1962 France ........................................ 203/90

OTHER PUBLICATIONS

Perry's Chemical Engineer's Handbook, 3rd Ed., 1950, pp. 1173-1175 & 1036 to 1039.
Hclabe & Smith, Unit Operations of Chemical Engineering, McGraw-Hill, 1956, pp. 367-368.

*Primary Examiner*—Hiram Bernstein

[57] ABSTRACT

Apparatus for solvent extraction of a mother liquor with a solvent that is immiscible with and has a different specific gravity than the mother liquor, is disclosed. Means are provided for introducing into an extraction chamber, the solvent, the mother liquor and a carrier gas. Such means simultaneously serve to atomize the solvent and the mother liquor and disperse same in the carrier gas whereby upon introduction a cloud phase is produced in the chamber.

The introducing and simultaneously atomizing is carried out through one and the same spray nozzle. Condensation means are arranged in the extraction chamber and function to terminate the cloud phase and produce a condensed extracted mother liquor phase and a condensed solvent phase containing the substance to be extracted. Means are provided for separating the condensed extracted mother liquor phase from the condensed solvent phase on the basis of the different specific gravities of same.

2 Claims, 1 Drawing Figure

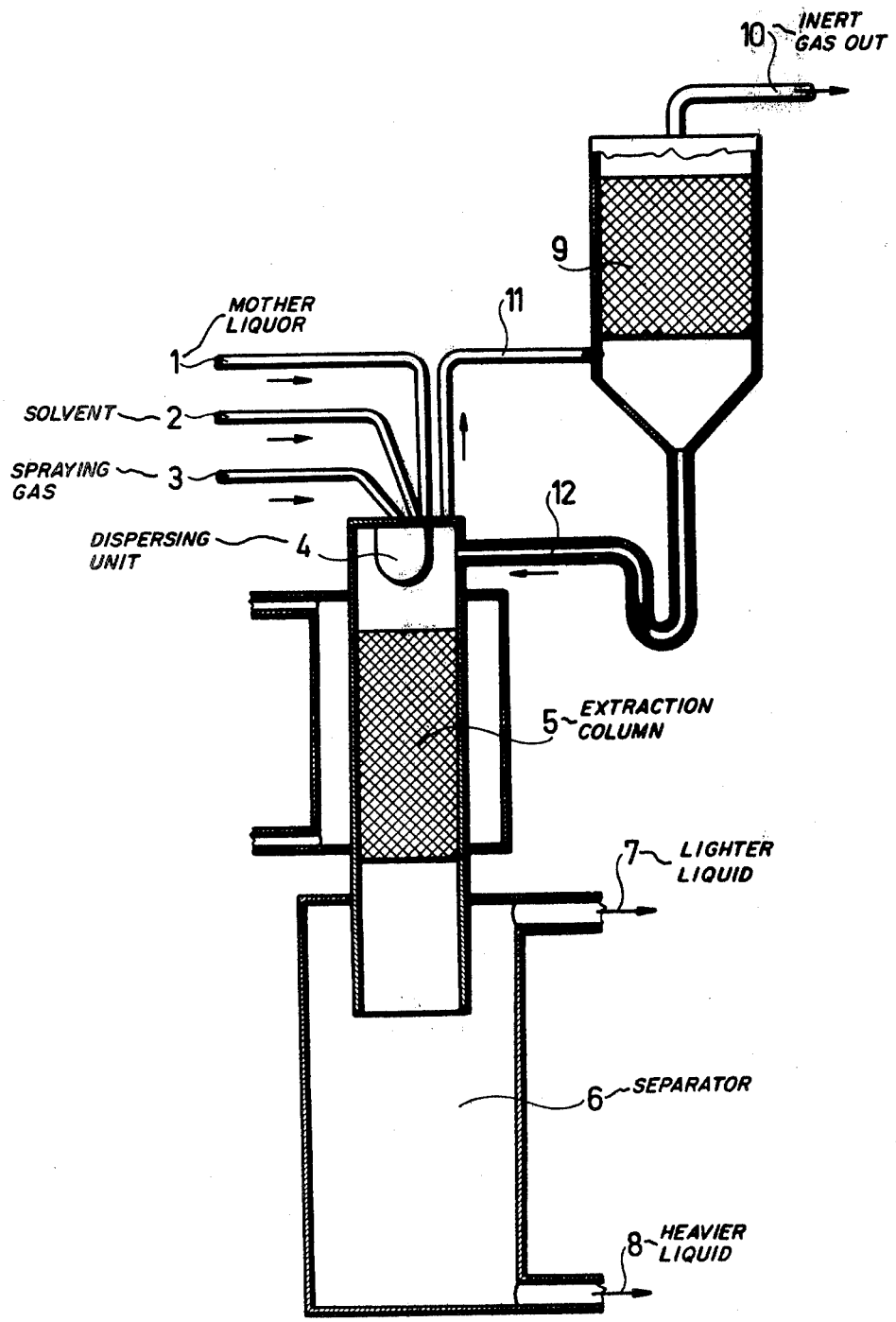

SOLVENT EXTRACTION APPARATUS

This is a continuation of application Ser. No. 633,172 filed Nov. 19, 1975, now abandoned, which in turn was a divisional of application Ser. No. 306,059, filed Nov. 13, 1972, which issued Feb. 3, 1976 as U.S. Pat. No. 3,936,489.

This invention relates to a process and an equipment for solvent extraction.

Solvent extraction is an operation known for a long time and widely utilized in every field of the industry. Material transport takes place in the liquid phase between two liquids which are mutually immiscible with each other, and may aim at the purification (or washing) of the so-called mother liquid, or at the enrichment or isolation of a valuable substance. Isomers of similar chemical characteristics but of different solubility can also be separated from each other by solvent extraction.

Solvent extraction is widely used in the chemical, pharmaceutical and food industries, in the preparation of drugs and cosmetics, and in numerous other branches of industry.

Using the different known methods and apparatus, new contact surfaces are created, i.e. the interface is renewed by difforming or dispersing one liquid in the other. Difforming and dispersing is carried out in the different equipments generally with the condition that a suppressable (i.e. breakable) difform or disperse system (emulsion) should be formed.

The common feature of the well known extraction equipments (such as spraying columns, Scheibel column, perforated plate columns, pulsating columns, apparatus for mixer-settler processes, centrifugal extractors, etc.) is that they difform or disperse one liquid in the other. More rapid material transport is attained by the renewal of the contact surfaces during difforming or dispersing.

According to the known processes extraction is carried out in one or several stages; generally large apparatus is employed which has large horizontal (columns) or vertical (mixer-settlers) dimensions, and both the mother liquor and the solvent reside in such apparatus for considerably long periods. On the other hand, centrifugal extractors, where a shorter residence time is also sufficient, require, due to their high rate of revolution, rotors made of special materials and at a high level of technology, excellent bearing support and careful operation. Moreover, in such equipments serious breakdowns may occur due to careless handling.

When using prior art apparatus, the extraction of sensitive, labile substances can be carried out only with great difficulty, partly due to the long residence times. Thus, for example, serious problems arise when the impurities (starting substances, by-products, etc.) to be removed from the mother liquor, i.e. from the main product of the chemical process, are highly water-soluble, but at the same time the mother liquor also reacts with water, i.e. it suffers hydrolysis. In such instances the residence time comes into the prominence, which, however, influences the extraction efficiency in a reverse way. In other words, the effective purification and acceptable materials transport require long residence time, while in order to suppress hydrolysis the residence time should be decreased.

Now we have found that the operation time as well as the contact time of the liquid pair can considerably be shortened without decreasing the extraction efficiency and the extent of material transport, and furthermore the extent of material transport compared to that of the known processes substantially increases, if the mother liquor and the solvent(s), mutually immiscible with each other and having a different specific gravity, are dispersed together in a gas. The fact that material transport proceeds with a higher rate and the extraction efficiency substantially increases when both the mother liquor and the solvent are dispersed in a gas and extraction is carried out in cloud phase is particularly striking and could not be aforeseen on the basis of the known art.

Examining several liquid pairs we have stated that when both the mother liquor and the solvent are brought into cloud phase and said cloud phase is subsequently terminated or destroyed and the liquids are separated from each other, a very short operation period as well as a particularly advantageous material transport and extraction efficiency can be attained. This short operation period is particularly advantageous where labile substances (mother liquor or extract) are concerned.

A further advantage of the short operation period is that the process can also be carried out at a temperature different from (lower or higher than) room temperature, since the temperature of the small volumes of liquids processed at a given moment can easily and safely be controlled. This advantage makes also possible to extend the use of extraction to substances which could not be worked up so far with the conventional extraction processes.

We have found, in a complete contradistiction with the prior art, that the mother liquor-solvent cloud phase of high disperison grade (order of magnitude of microns) can readily be destroyed with or without contracting it with a charge of high surface area, and the condensed liquids can be easily separated from each other.

The invention is a process for the solvent extraction of liquids mutually immiscible with each other and having different specific gravity, in which both the mother liquor and the solvent(s) are dispersed in a gas, thereafter the disperse system is destroyed by condensation, and the immiscible phases are separated from each other.

A further advantage of the process according to the invention is that substances sensitive to oxidation can be easily extracted using an inert gas, e.g. nitrogen or carbon dioxide, as dispersing medium. Another advantage is that the mother liquor-solvent ratio depends exclusively on the quantity and distribution coefficient of the substance to be extracted; consequently the substance that is to be recovered can be separated with a small amount of an appropriate solvent even from large quantities of a mother liquor.

According to the method of the invention the disperse system, i.e. the cloud phase, can be formed from the liquid pair by atomizing, such as by spraying.

The schematic picture of apparatus for realizing the above process is shown on the attached drawing. The invention also relate to this apparatus.

The dispersing unit 4, i.e. a spraying nozzle such as circular slit or slit nozzle, is attached to the top of the extraction column 5. The mother liquor enters the dispersing unit through line 1, the solvent through line 2, while when spraying is carried out with an inert gas, this gas is led to the dispersing unit through line 3. The extraction column 5 is optionally filled with a charge of high specific surface area (Raschig-rings, glass fibers, etc.) The inert gas leaving the column at the top enters the trap 9 through line 11, and leaves the same through line 10, while the liquid accumulated in trap 9 is recycled into the column through line 12.

Upon passing through the optionally charged column the cloud phase becomes destroyed, and the resulting liquid phase enters the separator 6. In this unit the liquids, due to their different specific gravities, separate from each other, and the heavier one leaves the separator through line 8, while the lighter one through line 7.

The extraction column 5 is jacketed. The most suitable temperature for the individual extraction processes can be ensured by circulating a cooling or heating medium in said jacket.

Most suitably the temperature of the column is adjusted to a temperature which is above the solidification point of the liquid having the highest solidification point and below the boiling point of the liquid having the lowest boiling point. Multiple step extraction apparatus can be constructed by connecting a number of the above-described apparatus in series. In such series-connected apparatus the liquid can be circulated in con-current or counter-current flow.

In the case of con-current extraction, line 7 of the first stage is connected with line 1 or 2 of the second stage, while line 8 of the first stage with line 2 or 1 of the second stage. The liquids leaving the second stage can similarly be fed into the third stage, and so on.

In the case of counter-current extraction, fresh mother liquor is fed into the first stage through line 1, and is dispersed together with a solvent obtained from line 8 or 7 of the second stage, taken already part in the extraction, entering the first stage through line 2. The solvent leaving the separator of the first stage is discarded, while the mother liquor is fed into line 1 of the second stage, and dispersed together with the solvent obtained from the separator of the third stage, entering the second stage through line 2. The solvent leaving the separator of the second stage is fed into line 2 of the first stage, while the mother liquor is pumped into line 1 of the third stage. Using a three-stage equipment fresh solvent is fed into line 2 of the third stage, the solvent obtained in the separator of the third stage is fed into the second stage, while the extracted mother liquor leaving the third stage is discarded.

Due to the short operation period (about 30 to 35 minutes) the dimensions of the apparatus may be relatively small even if high capacity is required. Consequently, such apparatus can be built with low costs even when the special tasks of certain extraction procedures require expensive construction materials (glass, stainless steel, etc.). This advantage is particularly important in several fields of pharmaceutical, food and chemical industry, where special extraction conditions are required.

The apparatus of the present invention does not contain moving elements, consequently it can be operated with good security, and the risk of breakdown is very low.

The process and the apparatus according to the invention can be used with great advantage for the separation of the individual components of isomeric mixtures, of liquids forming azeotropic mixtures, and of solutions, as well as for the extraction (purification or separation) of mother liquors or substances subject to decomposition.

The invention is further illustrated by the aid of the following non-limiting Examples.

The main characteristics of the glass equipment used in the Examples are as follows:

Extraction column: a jacketed glass column (outer diameter: 120 mm., inner diameter: 95 mm., length: 1000 mm.), is filled with Raschig-rings of 20 mm. diameter for a height of 600 mm. A circular-slit nozzle was used for dispersing. The dimensions of the separator are the same as of the extraction column.

EXAMPLE 1

Alkyl chloroformates and dialkyl carbonates are prepared in the presence of an excess of alcohol in a known manner. The obtained crude alkyl chloroformates contain 10 to 40% of alcohol, depending on the number of carbon atoms. Alcohol was removed by aqueous washing in a known manner, but due to the hydrolysis of alkyl chloroformates and dialkyl carbonates, a loss of 8 to 15% occurred even if washing was carried out with ice water.

4000 g./hour of crude methyl chloroformate (containing 39.6% by weight of methanol) and 4000 g./hour of water are sprayed into the extraction column described above with air of a pressure of 0.2 att. The residence time of the substance in cloud phase of 14° C. is 1.5 min. in the extractor and 30 min. in the separator.

After the first washing 2328 g./hour of methyl chloroformate containing 0.5% by weight of methanol, as well as 5672 g./hour of water containing 29.6% by weight of methanol leave the equipment.

The ester leaving the first stage is subjected to a second aqueous washing at 14° C. in an equipment guite similar to that used in the first stage.

The purity grade of the 3880 g./hour of methyl chloroformate leaving the second stage is 99.98% by weight, while the methanol content of the water is 0.49% by weight.

Extraction loss: 3.7% by weight of methyl chloroformate.

EXAMPLE 2

One proceeds as described in Example 1 with the difference, that 4000 g./hour of water of 0.95 att. pressure are used to disperse the crude methyl chloroformate. The temperature of the extraction column is 16° C., while the residence period in the column is 1.5 min. 2390. g./hour of methyl chloroformate containing 0.7% by weight of methanol, as well as 5600 g./hour of water containing 27.6% by weight of methanol are removed from the first stage. The second stage supplies 3919 g./hour of pure (methanol-free) methyl chloroformate and 4090 g./hour of water containing 0.58% by weight of methanol.

Extraction loss: 2% by weight of methyl chloroformate.

EXAMPLE 3

4000 g./hour of crude ethyl chloroformate (containing 21.2% by weight of ethanol) are fed into the first stage together with 4000 g./hour of water, and sprayed with air of a pressure of 0.2 att. The temperature of the extraction column is kept at 15° C. The residence time of the mixture is 1.5 min. in the extractor and 30 min. in the separator.

In the first stage 3220 g./hour of ethyl chloroformate containing 0.4% by weight of ethanol and 4880 g./hour of water containing 19.6% by weight of ethanol are obtained.

The second stage supplied 3900 g./hour of pure (ethanol-free) ethyl chloroformate and 4090 g./hour of water containing 0.39% by weight of ethanol.

Extraction loss: 2.3% by weight of ethyl chloroformate.

EXAMPLE 4

4000 g./hour of crude ethyl chloroformate, containing 21.2% by weight of ethanol, are dispersed into the first stage with 4000 g./hour of water of a pressure of 0.95 att. The temperature of the extraction column is kept at 17° C. The residence time of the mixture is 1.5 min. in the column and 30 min. in the separator. In the first stage 3160 g./hour of ethyl chloroformate containing 0.5% by weight of ethanol and 4840 g./hour of water containing 17.4% by weight of ethanol are obtained.

The second stage supplies pure (ethanol-free) ester and an aqueous phase containing 0.49% by weight of ethanol.

Extraction loss: 1.2% by weight of ethyl chloroformate.

EXAMPLE 5

4000 g./hour of isopropyl chloroformate containing 15% by weight of isopropanol and 4000 g./hour of water are sprayed into the first stage with air of a pressure of 0.2 att. The temperature of the extractor is kept at 14° C. The residence time is 1.5 min. in the column and 30 min. in the separator. The isopropyl chloroformate leaving the first stage contains 0.2% by weight of isopropanol, while the isopropanol content of the aqueous wash is 14.3% by weight. After the second stage 3913. g./hour of pure (alcohol-free) isopropyl chloroformate and 4087 g./hour of water containing 0.1% by weight of isopropanol are obtained.

Extraction loss: 2.1% by weight of isopropyl chloroformate.

EXAMPLE 6

One proceeds as described in Example 5 with the difference that the mixture is dispersed with water of a pressure of 0.95 att. The isopropyl content of isopropyl chloroformate leaving the first stage is 0.4%, while that of the aqueous wash is 13.6% by weight.

After the second stage 3927 g./hour of pure isopropyl chloroformate are obtained.

Extraction loss: 1.1% by weight.

EXAMPLE 7

4000 g./hour of crude diethyl carbonate (purity grade: 80.5% by weight) and 4000 g./hour of 10% aqueous sodium chloride solution are sprayed into the extraction column with air of a pressure of 0.2 att. (Saline is used in order to secure the necessary difference of specific gravity). Extraction is carried out at a temperature of 18° C. and with a residence time of 1.5 min. From the first stage 3258 g./hour of diethyl carbonate containing 1.5% by weight of ethanol are obtained.

The purity grade of diethyl carbonate leaving the second stage is 99.5% by weight, while after the third stage 3908 g./hour of practically pure diethyl carbonate are obtained.

Extraction loss: 2.5% by weight of diethyl carbonate.

EXAMPLE 8

The fed quantities are the same as indicated in Example 7, but the mixtures are dispersed with a 10% aqueous sodium-chloride solution of a pressure of 0.95 att. in all of the three columns.

The extraction temperature of the individual columns is 18° C., while the residence time is 1.5 min. in each of the columns and 30 min. in each of the separators.

After the third stage completely pure diethyl carbonate is obtained.

The aqueous phase leaving the first stage contains 15.6% by weight, that leaving the second stage 0.4% by weight, while that leaving the third stage 0.23% by weight of ethanol.

Extraction loss: 1.53% by weight.

EXAMPLE 9

6000 g./hour of a 30% aqueous acetic-acid solution and 2400 g./hour of isopropyl ether are sprayed into the first extraction column with air of a pressure of 0.2 att. After the first washing the acetic-acid content of the aqueous phase is 27.5%, and the amount of extract is 5640 g./hour.

The obtained raffinate is extracted again with 2400 g./hour of isopropyl ether in the same equipment. After this second stage 5190 g./hour of raffinate are obtained, containing 22.2% of acetic acid. This raffinate is extracted again with 2400 g./hour of isopropyl ether. 4663 g./hour of a raffinate containing 14.3% of acetic acid are obtained.

The percentage composition of the individual extracts obtained in the three extraction steps is in a good agreement with the calculated one, within the titration error limits.

What we claim is:

1. An apparatus for solvent extraction of a mother liquor with a solvent immiscible with and having a different specific gravity than the mother liquor, comprising an extraction chamber; means for introducing the solvent, mother liquor, and a carrier gas into the chamber and, simultaneously atomizing the solvent and the mother liquor and dispersing same in the carrier gas to produce in said chamber a cloud phase, said means for introducing and atomizing being a spray nozzle, the introduction into the chamber of the atomized solvent and mother liquor dispersed in the carrier gas being through one and the same spray nozzle, neither the solvent nor the mother liquor being atomized prior to said step of introducing and simultaneously atomizing means for separately conducting the solvent, the mother liquor and the carrier gas to the spray nozzle; condensation means arranged in said extraction chamber for terminating the cloud phase and producing a condensed extracted mother liquor phase and a condensed solvent phase containing the substance to be extracted; and means for separating the condensed extracted mother liquor phase from the condensed solvent phase on the basis of the different specific gravities of same.

2. The apparatus, as claimed in claim 1, wherein said nozzle is a circular slit or slit nozzle.

* * * * *